United States Patent
Bedoe et al.

(10) Patent No.: US 9,671,318 B1
(45) Date of Patent: Jun. 6, 2017

(54) SPECIMEN COLLECTOR

(71) Applicant: Medline Industries, Inc., Mundelein, IL (US)

(72) Inventors: Scott Bedoe, McHenry, IL (US); Taylor Ling, Buffalo Grove, IL (US); James Burgess, Lake Bluff, IL (US)

(73) Assignee: Medline Industries, Inc., Northfield, IL (US)

( * ) Notice: Subject to any disclaimer, the term of this patent is extended or adjusted under 35 U.S.C. 154(b) by 0 days.

(21) Appl. No.: 14/957,137

(22) Filed: Dec. 2, 2015

(51) Int. Cl.
*A61B 5/155* (2006.01)
*G01N 1/14* (2006.01)
*B01L 3/00* (2006.01)
*G01N 1/10* (2006.01)

(52) U.S. Cl.
CPC ............ *G01N 1/14* (2013.01); *B01L 3/502* (2013.01); *B01L 2300/042* (2013.01); *B01L 2300/0832* (2013.01); *B01L 2300/0848* (2013.01); *G01N 2001/1031* (2013.01)

(58) Field of Classification Search
CPC .. G01N 1/14; G01N 2001/1031; B01L 3/502; A61B 2010/0225; A61B 10/0045; A61M 1/0056; A61M 1/0001; A61F 2/02
See application file for complete search history.

(56) References Cited

U.S. PATENT DOCUMENTS

| | | |
|---|---|---|
| 743,091 A | 11/1903 | Loop |
| 2,115,577 A | 4/1938 | Goldman |
| 2,151,538 A | 3/1939 | Swanson |
| 3,788,484 A * | 1/1974 | Godin ............... B01D 29/012 210/447 |
| 3,855,997 A | 12/1974 | Sauer |
| D249,708 S | 9/1978 | Smith |
| D260,175 S | 8/1981 | Hein |
| 4,376,053 A * | 3/1983 | Bullock ............... A01J 5/0134 119/14.16 |
| 4,385,891 A | 5/1983 | Ligotti |
| D273,330 S | 4/1984 | Rouch |
| 4,443,220 A | 4/1984 | Hauer |
| 4,460,361 A | 7/1984 | Nichols |
| D285,606 S | 9/1986 | Christopherson |
| 4,643,197 A | 2/1987 | Greene |
| D305,934 S | 2/1990 | Sone |

(Continued)

FOREIGN PATENT DOCUMENTS

WO 2004075740 9/2004

OTHER PUBLICATIONS

Yeager, Anna et al.; Design U.S.Appl. No. 29/494,106, filed Jun. 17, 2014.

*Primary Examiner* — Paul Hyun
(74) *Attorney, Agent, or Firm* — Fitch, Even, Tabin & Flannery LLP

(57) ABSTRACT

A specimen collector includes a sleeve with one or more interior walls defining a substantially hollow interior cavity. The sleeve further includes an inlet port in fluid communication with the interior cavity and an outlet port in fluid communication with the interior cavity. The sleeve further includes a first side aperture and a second side aperture. The specimen collector also includes a tray slidable within the interior cavity of the sleeve. The tray includes a first specimen well and a second specimen well that alternately may be placed into fluidic communication with the inlet and outlet ports.

14 Claims, 7 Drawing Sheets

(56) References Cited

U.S. PATENT DOCUMENTS

| | | | |
|---|---|---|---|
| D306,340 S | 2/1990 | Whiting | |
| 4,957,492 A | 9/1990 | McVay | |
| 4,957,629 A | 9/1990 | Smith | |
| 5,042,979 A | 8/1991 | Anderson | |
| 5,049,273 A | 9/1991 | Knox | |
| 5,256,160 A * | 10/1993 | Clement | A61B 18/1482 220/502 |
| 5,387,339 A * | 2/1995 | Lee | B01D 33/067 210/321.89 |
| 5,409,024 A | 4/1995 | Morrison | |
| 5,514,119 A | 5/1996 | Curtis | |
| 5,624,418 A | 4/1997 | Shepard | |
| 5,797,742 A | 8/1998 | Fraker | |
| 5,817,032 A | 10/1998 | Williamson, IV | |
| 5,904,677 A | 5/1999 | Drummey | |
| 6,149,812 A | 11/2000 | Erickson | |
| D435,906 S | 1/2001 | Wilkinson | |
| 6,264,636 B1 | 7/2001 | Holm | |
| 6,375,625 B1 | 4/2002 | French | |
| D475,461 S | 6/2003 | Takagi | |
| 6,589,219 B1 | 7/2003 | Shibuya | |
| 6,733,664 B2 | 5/2004 | Menne | |
| D494,279 S | 8/2004 | Cogan | |
| 6,796,167 B2 | 9/2004 | Tigerholm | |
| 6,872,184 B2 | 3/2005 | Brannon | |
| D526,413 S | 8/2006 | Baker | |
| 7,083,761 B2 | 8/2006 | Zimmermann | |
| 7,244,236 B2 | 7/2007 | Merkle | |
| 7,449,106 B2 | 11/2008 | Ramsey | |
| 7,488,312 B2 | 2/2009 | Rogers | |
| 7,497,340 B2 | 3/2009 | Hershberger | |
| 7,572,236 B2 | 8/2009 | Quick | |
| 7,758,515 B2 | 7/2010 | Hibner | |
| 7,758,556 B2 | 7/2010 | Perez-Cruet | |
| 7,981,051 B2 | 7/2011 | Quick | |
| 8,088,079 B2 | 1/2012 | Kaye | |
| 8,088,291 B2 | 1/2012 | Hershberger | |
| 8,100,874 B1 | 1/2012 | Jordan | |
| 8,366,694 B1 | 2/2013 | Jordan | |
| 8,465,439 B2 | 6/2013 | Parks | |
| D690,826 S | 10/2013 | Kuroda | |
| 8,801,682 B2 | 8/2014 | Kensy | |
| 8,845,605 B2 | 9/2014 | Hensler | |
| 8,858,518 B2 | 10/2014 | Schafer | |
| 8,920,393 B2 | 12/2014 | Hensler | |
| D731,672 S | 6/2015 | Kuroda | |
| 9,220,485 B2 | 12/2015 | Parks | |
| D755,922 S | 5/2016 | Sherman | |
| 9,332,969 B2 | 5/2016 | Han | |
| 9,358,327 B1 | 6/2016 | Venturi | |
| 2003/0086830 A1 | 5/2003 | Haywood | |
| 2004/0087918 A1 | 5/2004 | Johnson | |
| 2007/0038146 A1 | 2/2007 | Quick | |
| 2011/0106029 A1 | 5/2011 | Garren | |
| 2011/0262405 A1 | 10/2011 | Segina | |
| 2015/0359949 A1 | 12/2015 | Yeager | |

* cited by examiner

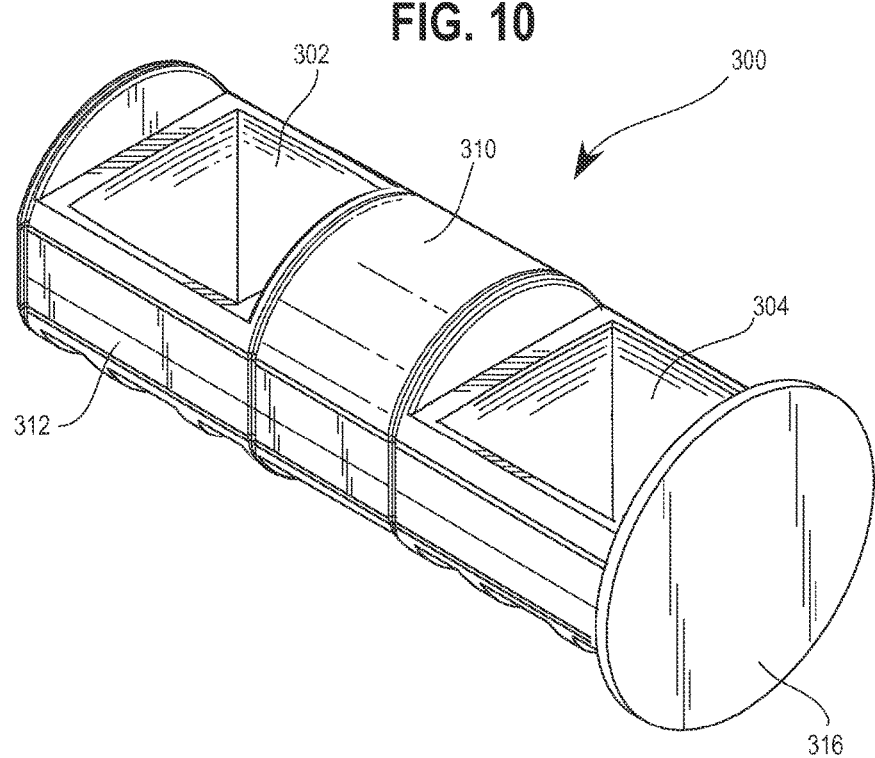
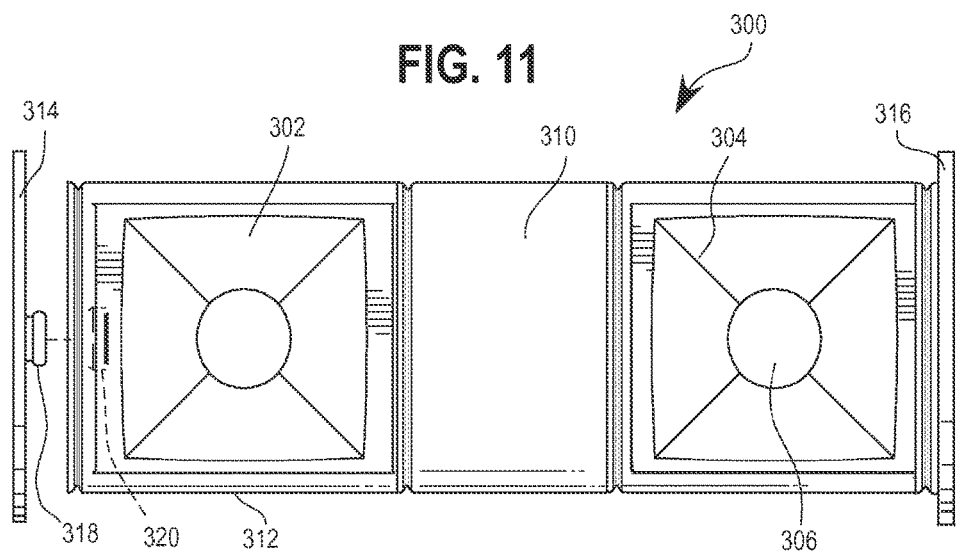

SPECIMEN COLLECTOR

TECHNICAL FIELD

The present disclosure generally relates in some aspects to a specimen collector and in other aspects to methods for collecting multiple specimens using a specimen collector. The specimens collected by the collector may for example be tissue samples, and more specifically, polyps.

BACKGROUND

In many surgical procedures, specimens are removed from a body and are collected so that they may be later analyzed. An example of such a specimen is a polyp. A polyp is an abnormal growth projecting from the wall of a body cavity. In the human body, polyps typically occur in the gastrointestinal tract, most commonly in the colon and rectum, but also in the nose, throat, and bladder.

Polyps may be precursors to cancers or may actually contain cancers. For this reason, once discovered, polyps are typically resected through a procedure known as a polypectomy. During the procedure, a polyp is detached from the cavity wall and extracted for subsequent examination, commonly using suction. Typically, the suction force is applied through an endoscope or other instrument that is fluidically coupled to a collection tank.

To separate a resected polyp from other material aspirated from the body, a polyp trap is often used. In some examples, the polyp traps are single-chamber traps that have inlet and outlet ports that are in axial alignment with the suction line. Conventionally, upon collecting a specimen in such trap, a user must remove the specimen prior to collecting another specimen, requiring disassembly of the trap and disconnection from the suction line, thereby causing a delay in the procedure. Polyp traps that include multiple chambers also are known. Some such polyp traps typically include a rotatable cap that allows a user to selectively deposit a specimen in various ones of the multiple chambers. Even for these traps, once all of the chambers have been filled with specimens, the polypectomy procedure must be paused to remove the specimens from the polyp trap or possibly to replace a portion of the trap assembly.

To address the above, a specimen collector with multiple chambers is now provided. In one approach, the specimen collector includes a sleeve that comprises one or more interior walls defining a substantially hollow interior cavity. The sleeve further includes inlet and outlet ports in fluid communication with the interior cavity. The sleeve also includes a first side aperture and a second side aperture preferably disposed in substantial axial alignment with the first side aperture. The specimen collector also includes a tray that is slidable within the interior cavity and that is captive in ordinary use. The tray includes a first specimen well and a second specimen well each separately positionable to be in a suction pathway defined by the inlet and outlet ports. In use, suction is applied to the outlet port and the inlet port is placed into fluidic connection with bodily matter to thereby draw the bodily matter into the specimen collector. The first specimen well is positioned within the interior cavity of the sleeve and in the suction pathway, and the second specimen well is positioned out of the suction pathway and preferably exterior to the interior cavity of the sleeve. Upon collection of a first specimen in the first specimen well, the tray is moved to place the second well into the suction pathway, and the first well is placed out of the suction pathway and preferably exterior of the cavity. The first specimen then may be removed and a second specimen collected in the second well without stopping the procedure. Also provided in some embodiments are methods of use of the specimen collector and methods of manufacture of the specimen collector.

Further aspects of the disclosure are described herein and illustrated in the appended drawings.

BRIEF DESCRIPTION OF THE DRAWINGS

FIG. 10 is a perspective view of the tray of the specimen collector shown in FIG. 2, shown before screens have been added and shown with an end cap removed.

FIG. 11 is a top plan view of the tray of FIG. 10 further depicting the removable end cap in partial exploded view.

References to "top" and other points of direction are for internal reference and are not intended to limit the orientation of the specimen collector in use. Skilled artisans will appreciate that elements in the figures are illustrated for simplicity and clarity and have not necessarily been drawn to scale. For example, the dimensions and/or relative positioning of some of the elements in the figures may be exaggerated relative to other.

DESCRIPTION

Figure 1:
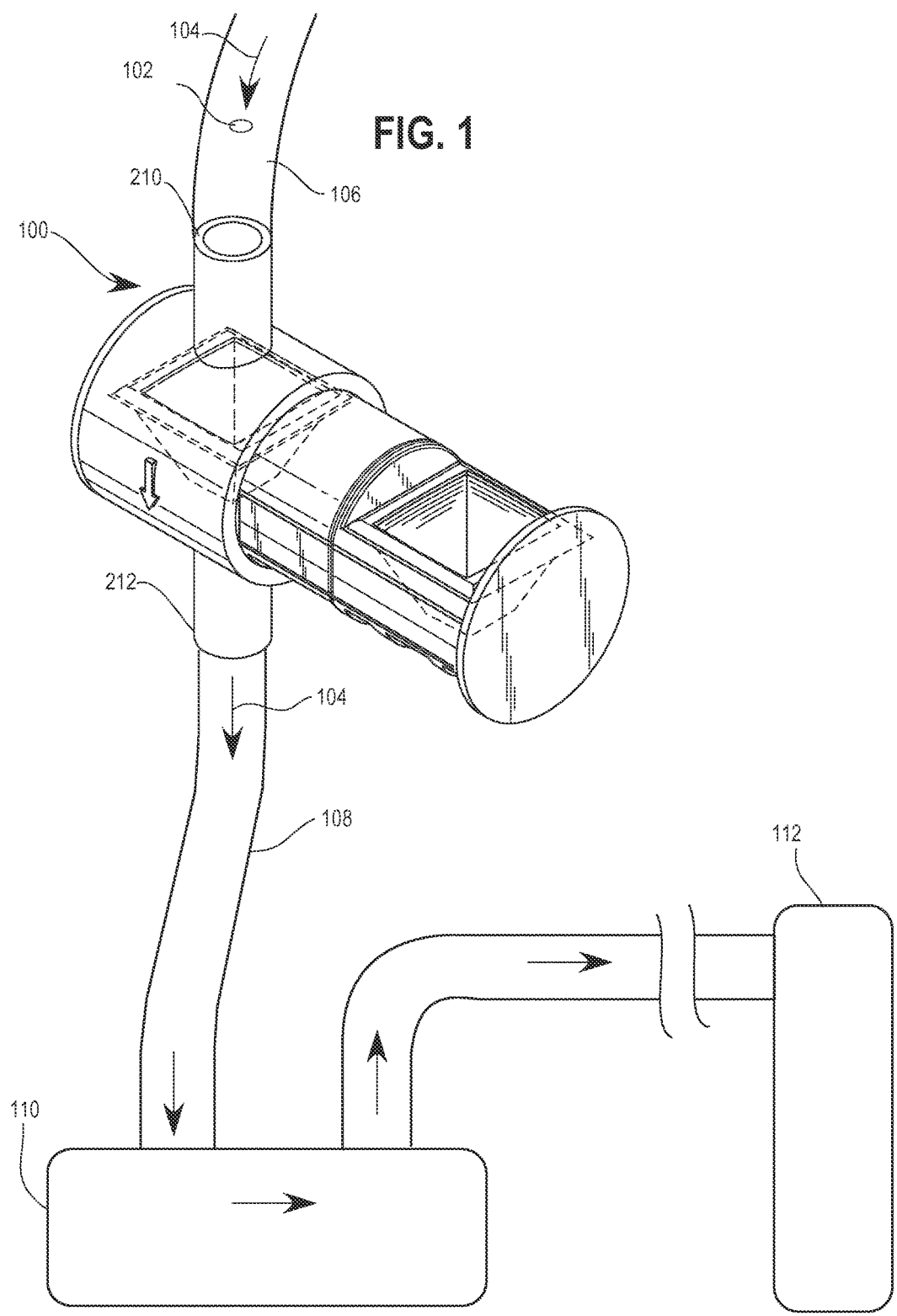
FIG. 1 is a view of a specimen collector connected to first and second suction tubes, and in fluid connection with a collection tank and a suction source.

Referring now to the drawings, and in particular to FIG. 1, a specimen collector 100 is configured to collect a specimen 102 removed from a body via a suction force that causes fluid to flow in the direction of arrow 104. The specimen collector 100 is connected at a first port 210 to a first tubular member 106 through which the specimen 102 and other fluids from a body pass due to the suction force 104. As discussed in greater detail elsewhere herein, the specimen collector 100 receives and traps the specimen 102.

The specimen collector 100 is also connected at a second port 212 to a second tubular member 108 that, due to suction force 104, transfers bodily fluids into a collection tank 110, thereby providing a suction pathway within the specimen collector. Suction is provided by a suction source 112.

Figure 2:
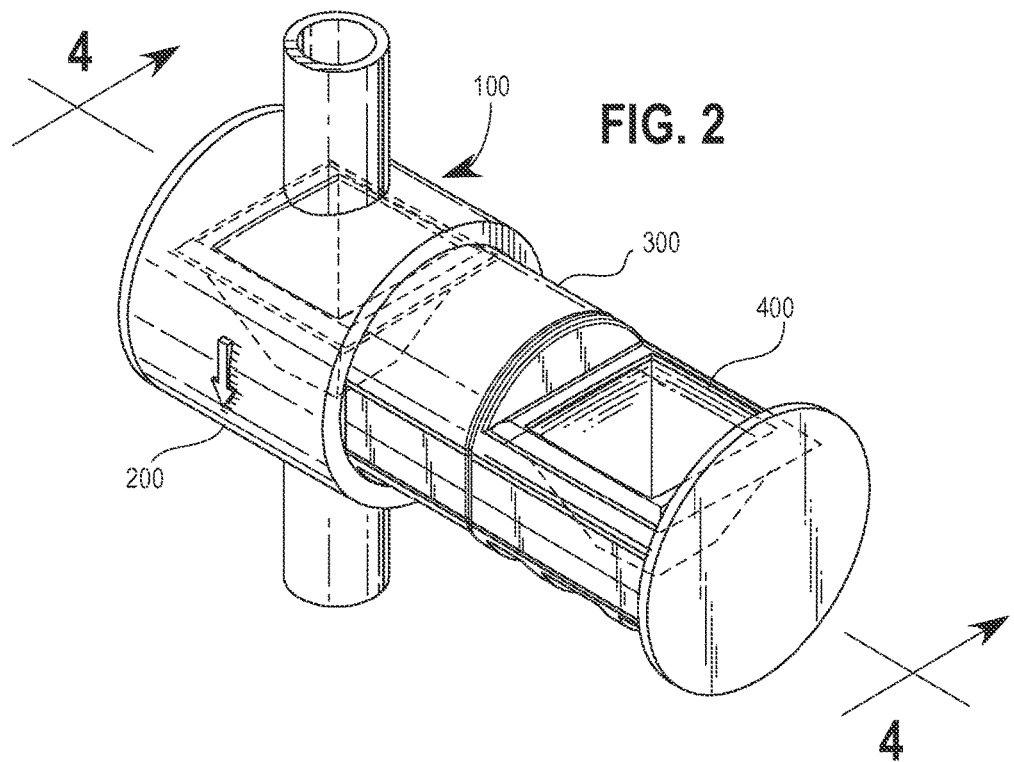
FIG. 2 is a perspective view of a specimen collector in accordance with one embodiment, the tray including screens disposed respectively in each well and showing the sleeve in a first position.
Figure 3:
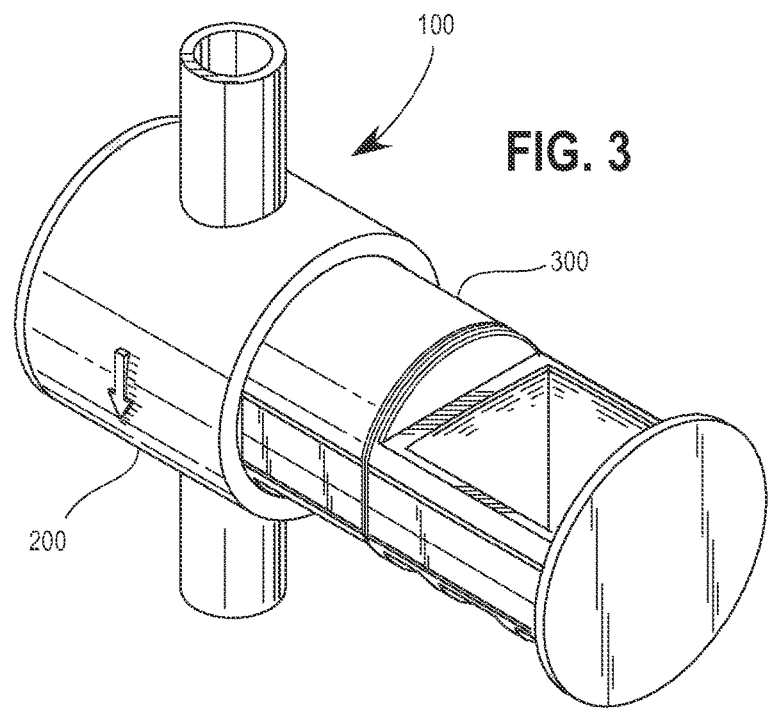
FIG. 3 is a perspective view of a specimen collector shown in FIG. 2, showing the tray before screens have been placed in the wells.

Referring now to FIGS. 2-5, the specimen collector 100 includes a sleeve 200 and a tray 300. The tray 300 is slidable within the sleeve 200. In this way, the tray 300 may be disposed in a first position, shown in FIG. 4, to receive a first specimen 102. The tray 300 may also be disposed a second position, shown in FIG. 5, whereby the tray is positioned to receive a second specimen 102'. As discussed in greater detail elsewhere herein, the tray 300 of the specimen collector 100 may also include one or more screens 400 disposed within wells of the tray 300, as shown in FIG. 2.

With further reference to the sleeve 200, and referring now to FIGS. 6-9, the sleeve 200 includes a sleeve body 202 having interior 204 and exterior 206 walls. The interior wall 204 defines a substantially hollow interior cavity 208 that is capable of receiving at least a portion of the tray 300.

In one approach, the interior 204 and exterior 206 walls have generally similar cross-sectional geometries. For example, as shown in FIGS. 6-9, the interior 204 and exterior 206 walls may both have circular cross-sectional geometries. In other approaches (not shown), the interior and exterior walls have dissimilar cross-sectional geometries. For example, the interior wall may have a polygonal cross-sectional geometry (e.g., triangular, quadrilateral, pentagonal, etc.), while the exterior wall may have a curved cross-sectional geometry (e.g., circular, oval, etc.), or vice-versa.

As heretofore stated, the sleeve 200 also includes an inlet port 210 and an outlet port 212 that are in fluid communication with the interior cavity 208 and that define a suction pathway (illustrated generally by arrow 104 in FIG. 9) therebetween. The inlet port 210 has an interior dimension sufficiently large to permit a resected specimen of expected size to pass therethrough, for example, a diameter of six millimeters. The interior dimension of the outlet port may be similar or dissimilar to that of the inlet port 210.

The ports 210, 212 preferably extend from the sleeve body 202, as illustrated, so as to enable connections with tubular members used to transport fluids and specimens from a body. The connections with the tubular members may be male-to-female or female-to-male. In other embodiments (not shown) one or both of the ports may be simple apertures or may extend inwardly. The inlet port 210 is disposed "upstream" of the interior cavity 208 such that fluids and specimens from a body travel through the inlet port 210 and into the interior cavity 208. The outlet port 210 is disposed "downstream" of the interior cavity 208 such that fluids and specimens from a body travel from the interior cavity 208 through the outlet port 212. As illustrated, the inlet port 210 may be disposed in axial alignment with the outlet port 212. In this way, the axes of each port are aligned at 180°. Alternatively, the ports may be disposed about along the exterior wall 218 to define a relative axial angle, the angle being, for example, less than 45°, between 45° and 90°, or greater than 90°. In some embodiments there may be no axial angle.

The sleeve 200 also includes a first side aperture 214 and a second side aperture 216. The first and second side apertures 214, 216 are dimensioned so as to permit a tray 300 in slidable engagement with the interior walls 204 of the sleeve body 202 to slide within the interior cavity 208. For example, where the tray 300 has an outer diameter of approximately 20 millimeters, the interior walls 204 of the sleeve body 202 may have a diameter of approximately 20.2 millimeters. The first and second side apertures 214, 216 are preferably in substantial axial alignment. In this way, the tray 300 is linearly slidable along a central axis of both the first aperture 214 and the second side aperture 216. Curved or other alternative configurations may be employed.

The distance between the first and second side apertures 214, 216 defines a depth of the interior cavity 208. This depth is sufficient to permit a specimen well of a tray (discussed in greater detail elsewhere herein) to be disposed within the interior cavity 208 of the sleeve 200. For example, the depth of the interior cavity 208 may be approximately 21 millimeters.

Figure 6:
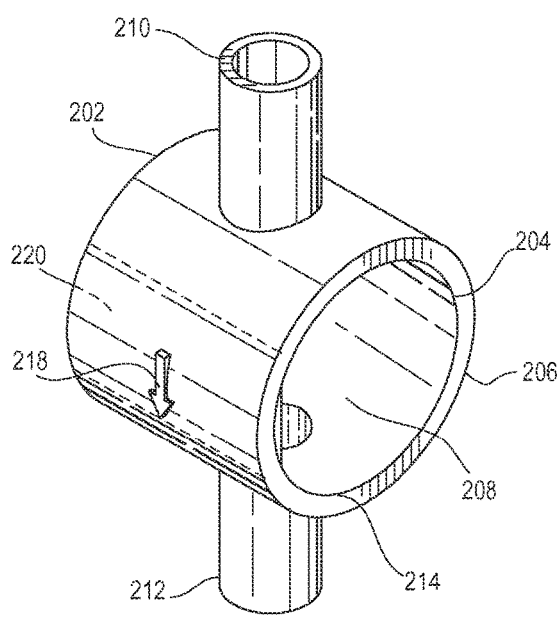
FIG. 6 is a perspective view of the sleeve of the specimen collector shown in FIG. 2.
Figure 7:
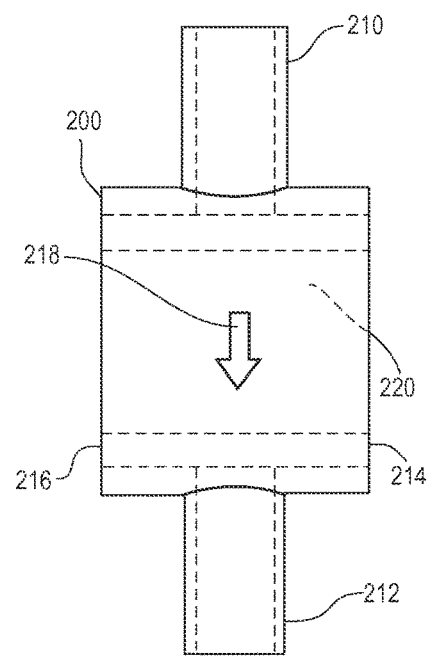
FIG. 7 is a front elevational view of the sleeve of FIG. 6.
Figure 8:
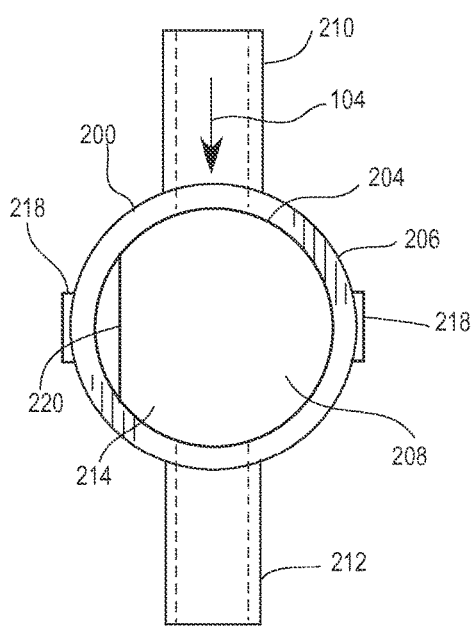
FIG. 8 is a side elevational view of the sleeve of FIG. 6.
Figure 9:
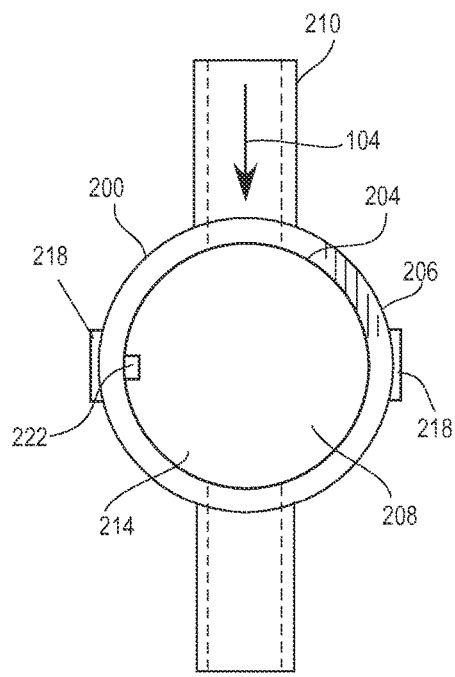
FIG. 9 is a side elevational view of an alternative sleeve embodiment depicting a guide rail.

The sleeve 200 may also include a visual or tactile orientation indicator that aids a user in orienting the sleeve 200 when connecting suction and drainage tubing. The orientation indicator may include words or raised symbols. For example, the sleeve may be provided with arrows 218 (FIGS. 6-10) pointing in the direction of the suction flow. The illustrated arrows are molded as raised features of the exterior wall 206 of the sleeve 200 to thereby provide both a visual and tactile orientation indication. Further, the sleeve may include one or more orientation surfaces that ensure correct placement of the tray into the sleeve or that maintain proper rotational orientation of the tray. The orientation surface may be a guide surface 220, as shown in FIGS. 6-8, that protrudes into the interior cavity 208 and that interfaces with a complementary surface 312 on the tray 300 (shown in FIGS. 10-13). The orientation surface may take any other suitable form. For example the orientation surface may comprise a recess (not shown) in the interior wall of the sleeve that receives a complementary protrusion disposed on the tray. In another example, as shown in FIG. 9, the orientation surface comprises a guide rail 222 that that protrudes into the interior cavity and that interfaces with a complementary groove on the tray. In yet another example, the interior cross-sectional geometry of the sleeve may be non-circular and complementary to the exterior cross-sectional geometry of the tray. For example, the interior cross-sectional geometry of sleeve may take a polygonal shape, and the exterior cross-sectional geometry of the tray may take a complementary polygonal shape. The complementary cross-sectional geometries serve to maintain a single rotational orientation of the tray with respect to the sleeve.

If the sleeve 200 is formed of a translucent or transparent material, then a user will be able to visually monitor fluid flow through the interior cavity 208, and to observe when a specimen 102 has entered the interior cavity 208. The sleeve 200 may also include a portion that includes magnification properties to further assist a user in observing activity in the interior cavity 208.

Figure 4:
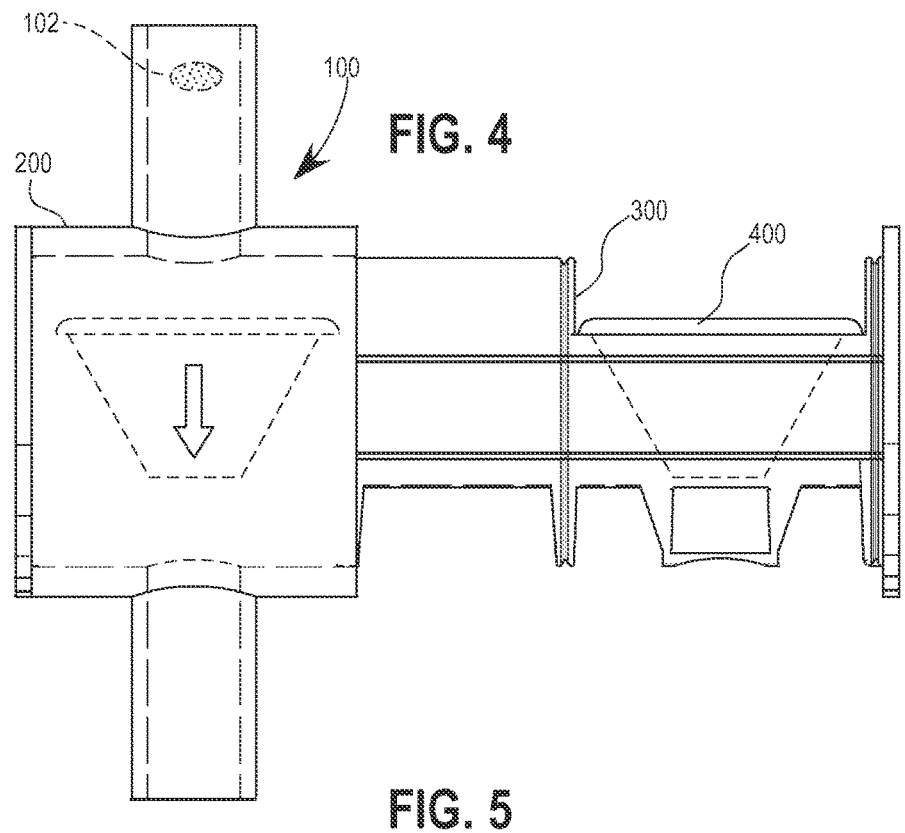
FIG. 4 is a cross-sectional view of the specimen collector of FIG. 2 taken along line 4-4' in FIG. 2.
Figure 5:
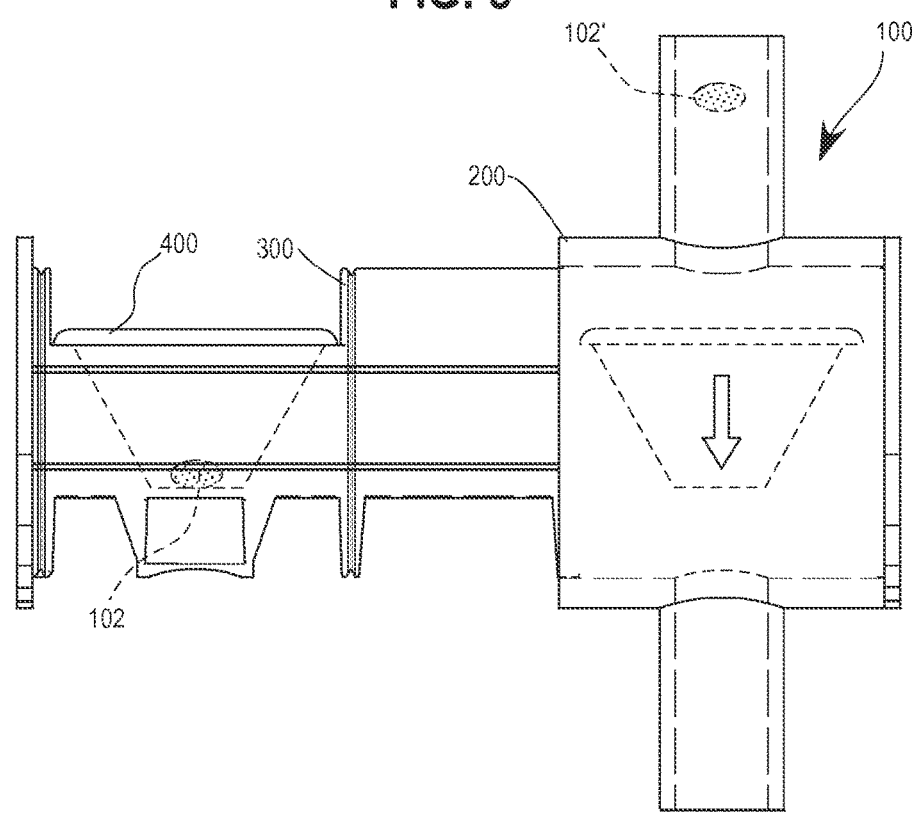
FIG. 5 is a cross-sectional view of the specimen collector of FIG. 2 showing the sleeve after it has been moved to a second position.

As discussed, the tray 300 is partially disposed within the interior cavity 208 of the sleeve 200. Referring now to FIGS. 10-13, the tray 300 includes a first specimen well 302 and a second specimen well 304, the wells being distributed axially along a central axis of the tray. In a first tray position, the first specimen well 302 is disposed within the interior cavity 208 and is in fluid communication with the inlet port 210 and the outlet port 212 of the sleeve 200. Also in this first position, the second specimen well 304 is disposed exterior to the interior cavity 208, as seen in FIG. 4. The tray 300 is slidable within the interior cavity 208 of the sleeve 200 such that the tray 300 may be slid into a second tray position. In this second position, the second specimen well 304 is disposed within the interior cavity 208 and is in fluid communication with the inlet port 210 and the outlet port 212 of the sleeve 200. Also in this second position, the first specimen well 302 is disposed exterior to the interior cavity 208. An example of a tray 300 in this second position is shown in FIG. 5.

The specimen wells 302, 304 may have any geometry suitable for retention and collection of specimens. In one approach, the first and second specimen wells 302, 304 are formed in a cup- or funnel-like shape. Such specimen wells 302, 304 may have a depth of between 8 millimeters and 12 millimeters, and more specifically, approximately 10 millimeters.

In the tray illustrated in FIG. 11, the bottom regions of the specimen wells 302, 304 have an opening 306 disposed therethrough to permit fluid communication through the specimen wells 302, 304. Such specimen wells 302, 304 may be configured to receive removable screens. Referring to FIGS. 14-17, a removable screen 400 rests within the specimen well and has a profile that is generally complementary to that of the corresponding specimen well. The screen 400 preferably has fluid-impermeable side walls 402 and a porous region, preferably positioned as bottom surface 404. By this is contemplated a surface that permits fluid communication therethrough but that is sized to retain polyps or other specimens. The porous surface may be, for example, a surface with multiple holes such as a screen or mesh surface with pores or screen openings sufficiently large enough to permit fluids to pass through, while also sufficiently small enough to prevent a specimen 102 from passing through. For example, the holes of a porous surface may have diameters of between 0.3 millimeters and 0.8 millimeters, and more specifically, approximately 0.5 millimeters. The screen may be otherwise configured; for example, portions of the walls of the screen may be porous and the bottom surface may be fluid-impermeable. The removable screen 400 may have a height of approximately 10 millimeters, a width of approximately 18 millimeters, and a depth of approximately 16 millimeters. In this way, the screen 400 is dimensioned so as to fit within a standard formalin container. The screen 400 may include a rim region 406 to assist in positioning and retaining the screen within the wells.

Figure 12:
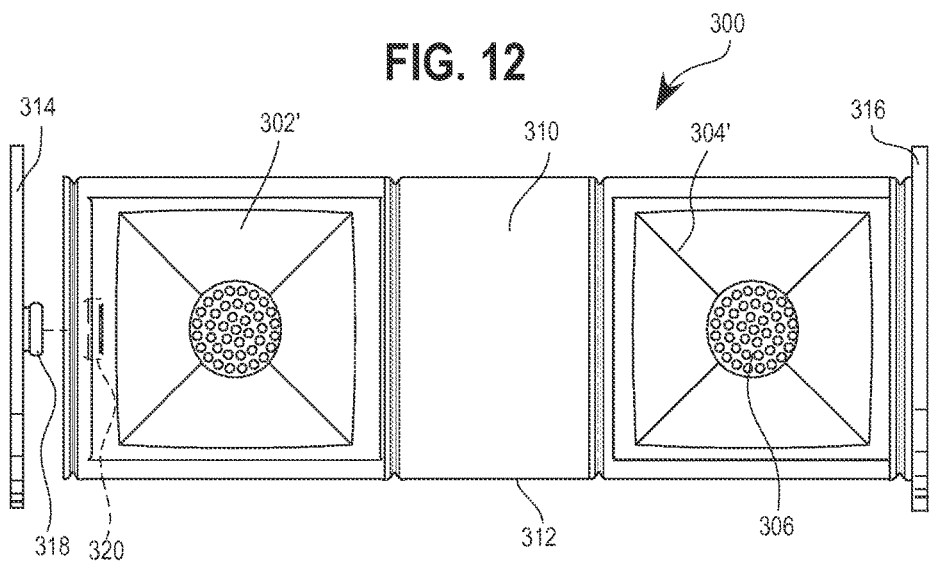
FIG. 12 is a top plan view of an alternative tray embodiment depicting wells with integral screen surfaces.
Figure 13:
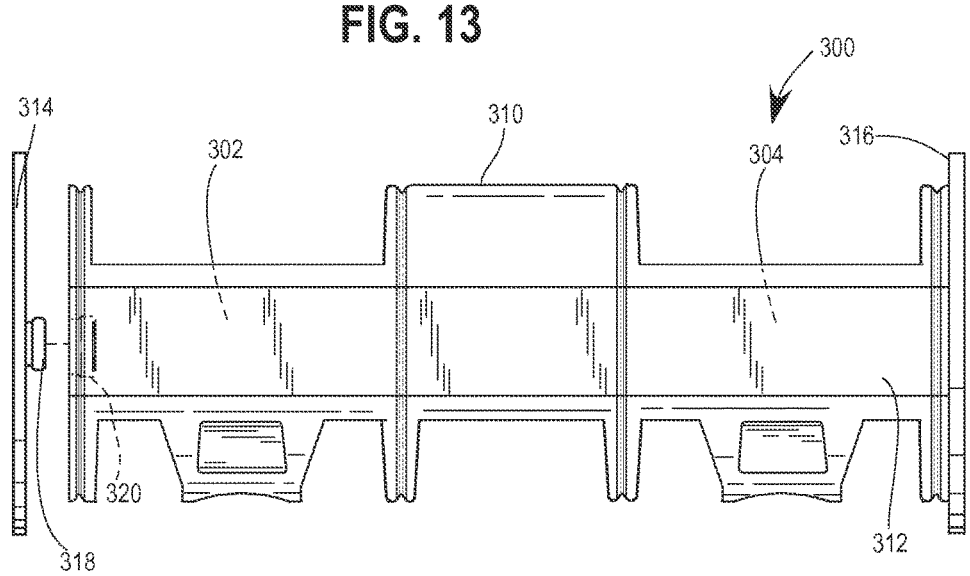
FIG. 13 is a front elevational view of the tray of FIG. 11.
Figure 14:
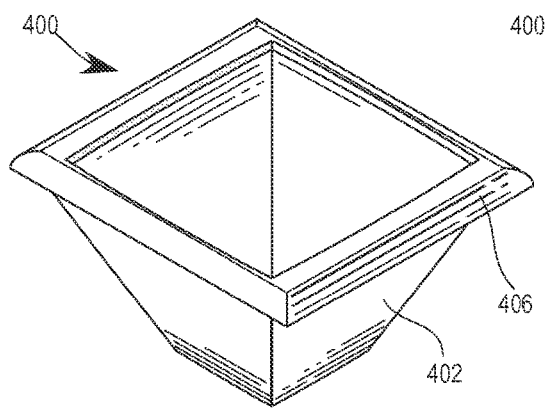
FIG. 14 is a perspective view of one of the screens of the specimen collector shown in FIG. 2.
Figure 15:
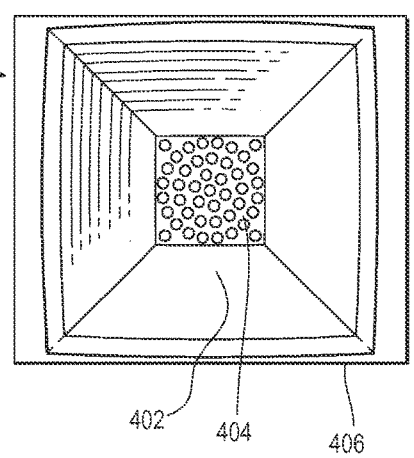
FIG. 15 is a top plan view of the screen of FIG. 14.
Figure 16:
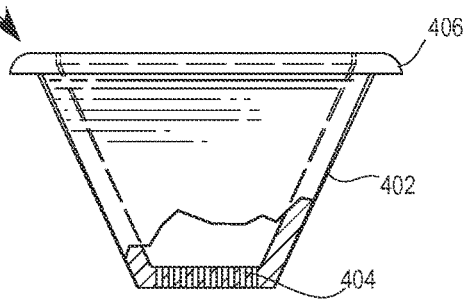
FIG. 16 is a partially cut away side elevational view of the screen of FIG. 14.
Figure 17:
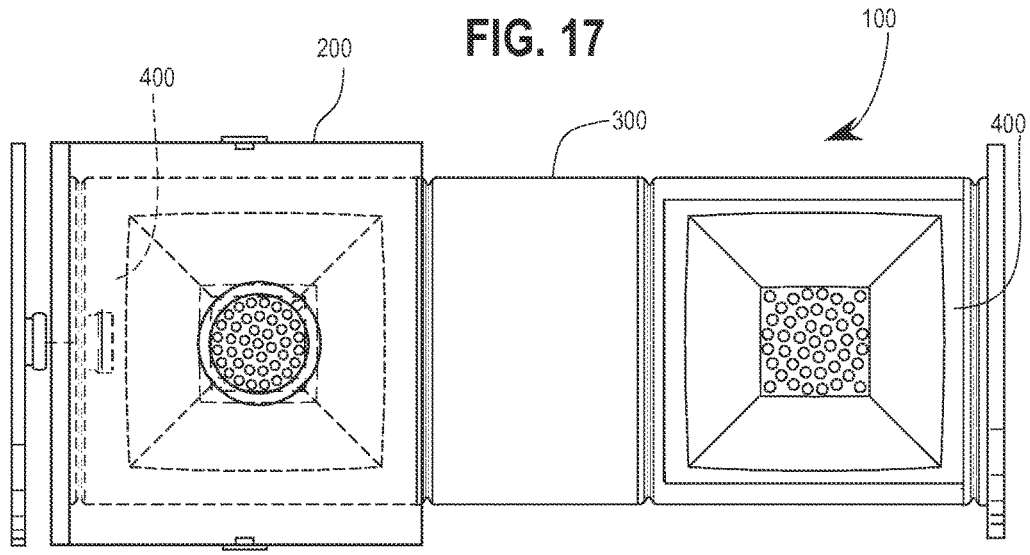
FIG. 17 is a top plan view of the tray of the specimen collector of FIG. 2, shown after screens have been placed into the wells.

Referring now to the alternative configuration depicted FIG. 12, instead of a bottom opening, the specimen wells 302', 304' may have an integral porous bottom surface 308' that permits fluid communication through the specimen wells 302', 304' while also preventing a specimen from passing therethrough. In this configuration, screens optionally may be used but are not necessary. The wells otherwise may be similarly configured to the wells 302, 304 as heretofore described.

Returning to FIGS. 10-13, the first specimen well 302 and the second specimen well 304 are preferably discrete specimen wells separated by a central tray region 310 disposed between the first specimen well 302 and the second specimen well 304. The central tray region may have any suitable size and configuration, and for example may have a thickness of between approximately 10 millimeters and 20 millimeters, and more specifically, approximately 15 millimeters. In the illustrated embodiment, the central tray region 310 comprises an impermeable surface. In this way, when the central tray region 310 is disposed within the interior cavity 208 and in alignment with the inlet port 210 of the sleeve 200, the central tray region 310 serves to prevent fluid communication between the inlet portion 210 and the outlet port 212. In an alternative approach, the central tray region may include an aperture (not shown) that permits direct fluidic communication between the inlet port and the outlet port when the aperture is in within the suction pathway. In still another approach, the central tray region may have axial extension that is less than the interior dimension of the inlet port (smaller than depicted). In this approach, a suction pathway would remain in place with no break in suction to the patient even during the process of moving the tray between the first and second provisions.

As heretofore described, the sleeve and tray may include cooperating orientation surfaces. With further reference to the tray 300 shown in FIGS. 10-13, the orientation surface may be a guide surface 312 that interfaces with a complementary surface of the sleeve 200 (e.g., guide surface 220). In another example, the orientation surface may be groove (not shown) that receives a guide rail (e.g., guide rail 222 of FIG. 9) of the sleeve 200. In another example, the orientation surface is a recess in the tray (not shown) that receives a protrusion disposed on the interior wall of the sleeve.

In yet another example, exterior cross-sectional geometry of the tray may be non-circular and complementary to the interior cross-sectional geometry of the sleeve. For example, the exterior cross-sectional geometry of the tray may take a polygonal shape, and the interior cross-sectional geometry of the sleeve of the tray may take a complementary polygonal shape. The complementary cross-sectional geometries serve to maintain a single rotational orientation of the tray with respect to the sleeve.

In a preferred approach, the tray 300 includes a first end cap 314 and a second end cap 316 disposed at opposing ends of the tray 300. The end caps 314, 316 occlude movement of the tray beyond the desired the motion pathway of the tray, with the extreme end positions of the tray constituting the first and second positions heretofore described. Both end caps may be detachable, but in some embodiments one of the end caps 316 is integrally formed with the remainder of the tray 300 (e.g. via injection molding or via ultrasonic welding) and the other end cap 314 is detachable from the tray 300 to allow for assembly. In one example, the end cap 314 is secured to the tray 300 via a snap-fit connection between a protrusion 318 extending from the end cap 314 and a complementary recess 320 in the tray 300. In another example (not shown), the end cap is secured to the tray via a threaded connection.

The sleeve 200 and the tray 300 are preferably formed of plastic materials, which each may be the same or different. For example, the sleeve 200 may be polypropylene, and the tray 300 may be polycarbonate. The use of different plastics having different rigidities is believed to assist in providing a sealing effect between the sleeve 200 and the tray 300. In another approach, a sealing effect may also be provided through the use of a gasket (not shown) disposed between the sleeve 200 and the tray 300.

As discussed herein, the tray 300 in certain approaches includes two specimen wells 302, 304 capable of being slidably positioned within a sleeve 200. In other approaches (not shown), the tray includes three or more specimen wells, which may be aligned along a central longitudinal axis of the tray or may be otherwise configured as appropriate. For example, the wells may be distributed radially about an annular tray. In this alternative approach, the circular tray is rotatably slidable through the interior cavity 208 of the sleeve 200.

The specimen collector may be used in any suitable medical procedure, by which is contemplated the inclusion of veterinary procedures. In use, after the screens have been installed into the wells where necessary, the specimen collector is connected to a source of suction at the outlet port via tubing and additional tubing is connected to the inlet port. When it is desired to collect a specimen, bodily fluid is introduced through the tubing connected to the inlet port and suction is applied to the outlet port to thereby create a suction pathway. The tray is disposed in the first position until a first specimen is obtained. Subsequently, upon retention of a specimen in the first well, the tray is slid to the second position and the first specimen is removed to thereby collect the specimen. Optionally the screen may be left in place or a new screen may be inserted, while suction continues. When a second specimen is collected, the tray may be moved back to the first position and the medical procedure continued as long as desired. There will be no need to stop the medical procedure and there will be minimal or no break in suction applied to the patient.

Also encompassed herein is a method of manufacture of a specimen collector. Generally, this method includes providing a sleeve and tray in accordance with one or more of the embodiments as heretofore described, inserting the sleeve into the tray, and connecting the end cap, and optionally further installing screens.

It is thus seen that an improved specimen collector and method of collecting multiple specimens are provided. Due in part to its relatively light weight, the specimen collector 100 may be disposed "in-line" between two tubing sections and does not need to be rested on a flat surface. Efficiency during a polypectomy procedure is also greatly increased. For example, due to reciprocating movement of the slidable tray 300, a polypectomy procedure does not need to be paused during removal of a specimen 102 from the tray 300. Rather, a first user may remove a first specimen (e.g., specimen 102) from the tray 300 while a second user continues to perform the polypectomy procedure, drawing a second specimen (e.g., specimen 102') into the tray 300. Furthermore, a user may slide the tray 300 from one position to another position with one hand, keeping the user's other hand free to remove a specimen 102 from the tray 300. The user is not limited in the number of specimens that may be collected before replacement of the assembly is required.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain approaches or embodiments as "preferred" approaches or embodiments, and other recitation of approaches, embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A specimen collector comprising:
    a sleeve comprising one or more interior walls defining a substantially hollow interior cavity, the sleeve further comprising:
        an inlet port in fluidic communication with the interior cavity;
        an outlet port in fluidic communication with the interior cavity; and
        first and second side apertures;
    a tray slidable within the interior cavity of the sleeve, the tray comprising a first specimen well and a second specimen well and movable between a first position wherein the first specimen well is in fluidic communication with the inlet and outlet ports and a second position wherein the second specimen well is in fluidic communication with the inlet and outlet ports.

2. The specimen collector of claim 1, wherein the second specimen well is disposed exterior to the interior cavity when the first specimen well is in fluidic communication with the inlet and outlet ports.

3. The specimen collector of claim 1, wherein the first specimen well is disposed exterior to the interior cavity when the second specimen well is in fluidic communication with the inlet and outlet ports.

4. The specimen collector of claim 1, wherein the inlet port and the outlet port are disposed in substantial axial alignment.

5. The specimen collector of claim 1, wherein the first and second side apertures are disposed in substantial axial alignment.

6. The specimen collector of claim 1, wherein the first specimen well and the second specimen well are distributed axially along a central axis of the tray.

7. The specimen collector of claim 1, wherein the first specimen well and the second specimen well include a porous surface to provide a fluid communication through the porous surface.

8. The specimen collector of claim 1, each well being provided with a removable screen, each screen comprising a fluid-permeable region.

9. The specimen collector of claim 1, wherein at least one of the one or more interior walls of the sleeve comprises an orientation surface configured to maintain a single rotational orientation of the tray with respect to the sleeve.

10. A method comprising:
    providing a sleeve comprising one or more interior walls defining a substantially hollow interior cavity, the sleeve further comprising:
        an inlet port in fluidic communication with the interior cavity;
        an outlet port in fluidic communication with the interior cavity; and
        first and second side apertures;
    providing a tray slidable within the interior cavity of the sleeve, the tray comprising a first specimen well and a second specimen well and movable between a first position wherein the first specimen well is in fluidic communication with the inlet and outlet ports and a second position wherein the second specimen well is in fluidic communication with the inlet and outlet ports.

11. A method according to claim 10, further comprising placing an end cap onto the tray.

12. A method comprising:
providing a specimen collector, the specimen collector comprising:
a sleeve comprising one or more interior walls defining a substantially hollow interior cavity, the sleeve further comprising:
   an inlet port in fluidic communication with the interior cavity;
an outlet port in fluidic communication with the interior cavity; and
first and second side apertures;
   a tray slidable within the interior cavity of the sleeve, the tray comprising a first specimen well and a second specimen well and movable between a first position wherein the first specimen well is in fluidic communication with the inlet and outlet ports and a second position wherein the second specimen well is in fluidic communication with the inlet and outlet ports;
applying suction to said outlet port and recovering bodily fluids through said inlet port;
upon retention of a specimen in the first well, sliding the tray to the second position; and
collecting the specimen from the first tray.

13. The method of claim 12, wherein sliding the tray to dispose the second specimen well in fluidic communication with the inlet port and the outlet port disposes at least a portion of the first specimen well and the received specimen exterior to the interior cavity of the sleeve.

14. The method of claim 12, further comprising:
receiving a second specimen in the second specimen well; and
sliding the tray to place the first specimen well back into fluidic communication with the inlet port and the outlet port.

* * * * *